United States Patent [19]
Wideman et al.

[11] Patent Number: 5,777,012
[45] Date of Patent: Jul. 7, 1998

[54] POLYSULFIDES OF N-METHYLPYRROLIDINONE

[75] Inventors: Lawson Gibson Wideman, Tallmadge; Shingo Futamura, Wadsworth, both of Ohio

[73] Assignee: The Goodyear Tire & Rubber Company, Akron, Ohio

[21] Appl. No.: 902,791

[22] Filed: Jul. 30, 1997

[51] Int. Cl.⁶ .............. C08J 5/24; C08G 63/91; C08G 2/16; C07D 207/12
[52] U.S. Cl. .............. 524/261; 524/418; 528/220; 525/55; 525/233; 525/240; 525/280; 525/326.5; 525/331.7; 525/471; 525/535; 525/540; 548/520
[58] Field of Search .............. 524/261, 418; 525/55, 233, 240, 280, 326.5, 331.7, 471, 535, 540; 528/220; 548/520

[56] References Cited

U.S. PATENT DOCUMENTS 4,482,663 11/1984 Kraus.

Primary Examiner—Robert W. Ramsuer
Assistant Examiner—Ebenezer Sackey
Attorney, Agent, or Firm—Bruce J. Hendericks

[57] ABSTRACT

The present invention relates polysulfides of N-methylpyrrolidinone and to rubber compositions containing such polysulfides. Addition of the polysulfides to rubber improves the hysteresis, accelerates the cure rate and improves filler dispersion.

11 Claims, No Drawings

POLYSULFIDES OF N-METHYLPYRROLIDINONE

BACKGROUND OF THE INVENTION

N-methylpyrrolidinone has been used to functionalize "living" lithium polymerized rubbers. The resulting modified rubbers have improved rubber-filler interaction. Unfortunately, many of the rubbers used commercially are not lithium polymerized and such techniques are limited to the "living" rubbers.

SUMMARY OF THE INVENTION

The present invention relates to compounds of the formula

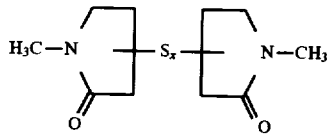    I where x is an integer of from 2 to 30; and rubbers containing such compounds.

DETAILED DESCRIPTION OF THE PREFERRED EMBODIMENT

There is disclosed compounds of the formula

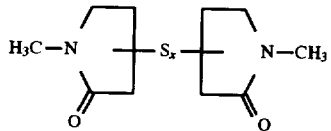    I where x is an integer of from 2 to 30. Preferably, x is an integer of from 3 to 15.

In accordance with an embodiment of the present invention, the level of polysulfides of Formula I in the rubber may vary. For example, the level may range from about 0.1 to about 10 parts by weight per 100 parts of rubber (also referred to herein as phr). Preferably, the level ranges from about 0.3 to about 3.0 phr.

The compounds of Formula I are prepared by reacting N-methylpyrrolidinone with sulfur monochloride. The reaction is preferably carried out in the presence of a halogen scavenger. Representative scavengers for the chlorine is triethylamine, trimethylamine and similar tertiary amines.

Depending on the desired integer for "x," the molar ratio of the N-methylpyrrolidinone to sulfur monochloride may vary. For example, the molar ratio of N-methylpyrrolidinone to sulfur monochloride may be as low as 2:1 to as high as 1:15. As can be appreciated, the more sulfur present relative to N-methylpyrrolidinone, the higher "x" will be. Preferably, the molar ratio of N-methylpyrrolidinone to sulfur monochloride ranges from 1:1 to 1:8.

The reaction should be conducted in the absence of oxygen and water. Preferably, the reaction is conducted in a nitrogen atmosphere and in an aprotic organic solvent. Suitable solvents which may be used include chloroform, dichloromethane, carbon tetrachloride, hexane, heptane, cyclohexane, xylene, benzene, dichloroethylene, dioxane, diisopropyl ether, tetrahydrofuran and toluene. Preferably, the solvent is toluene.

The reaction is exothermic; however, one may heat the reaction mixture to expedite the reaction rate. Generally speaking, the reaction is conducted at a temperature ranging from about 0° to 120° C.

In accordance with another embodiment, the present invention relates to a rubber composition comprising: (1) a natural and/or synthetic rubber and (2) from about 0.5 to about 10 phr of a compound represented by the formula:

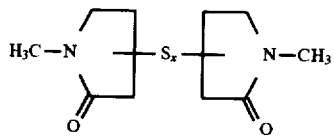    I where x is an integer of from 2 to 30.

For purposes of the present invention, the compounds of the above formula may be used to lower the hysteresis of a rubber (as measured by lower tan delta at 60° C.), increase the rate of cure of a rubber and improve the dispersion of a filler in rubber (as measured by lowered G' ratio of the compound). The polysulfide of Formula I is added to a sulfur vulcanizable elastomer or rubber. The term "sulfur vulcanizable elastomer or rubber" as used herein embraces both natural and all its various raw and reclaim forms as well as various synthetic rubbers. Representative synthetic polymers include the homopolymerization products of butadiene and its homologues and derivatives, as for example, methylbutadiene, dimethylbutadiene and pentadiene as well as copolymers such as those formed from butadiene or its homologues or derivatives with other unsaturated organic compounds. Among the latter are acetylenes, for example, vinyl acetylene; olefins, for example, isobutylene, which copolymerizes with isoprene to form butyl rubber; vinyl compounds, for example, acrylic acid, acrylonitrile (which polymerizes with butadiene to form NBR), methacrylic acid and styrene, the latter polymerizing with butadiene to form SBR, as well as vinyl esters and various unsaturated aldehydes, ketones and ethers, e.g. acrolein, methyl isopropenyl ketone and vinylethyl ether. Also included are the various synthetic rubbers prepared by the homopolymerization of isoprene and the copolymerization of isoprene and other diolefins in various unsaturated organic compounds. Also included are the synthetic rubbers such as 1,4-cis-polybutadiene and 1,4-cis-polyisoprene and similar synthetic rubbers.

Specific examples of synthetic rubbers include neoprene (polychloroprene), polybutadiene (including trans- and cis-1,4-polybutadiene), polyisoprene (including cis-1,4-polyisoprene), butyl rubber, halobutyl rubber copolymers of 1,3-butadiene or isoprene with monomers such as styrene, acrylonitrile and methyl methacrylate, as well as ethylene/propylene/diene monomer (EPDM) and in particular ethylene/propylene/dicyclopentadiene terpolymers. The preferred rubbers for use in the present invention are natural rubber, polybutadiene, polyisobutylene, EPDM, butadiene-styrene copolymers, cis-1,4-polyisoprene and polychloroprenes.

For purposes of the present invention, the term "sulfur vulcanized rubber" is used herein to describe the vulcanized reaction product of the above rubbers containing the polysulfides of N-methylpyrrolidinone.

In order to cure the rubber composition of the present invention, one adds a sulfur vulcanizing agent. Examples of suitable sulfur vulcanizing agents include elemental sulfur (free sulfur) or sulfur donating vulcanizing agents, for example, an amine disulfide, polymeric polysulfide or sulfur olefin adducts. Preferably, the sulfur vulcanizing agent is elemental sulfur. The amount of sulfur vulcanizing agent will vary depending on the type of rubber and the particular type of sulfur vulcanizing agent that is used. Generally speaking, the amount of sulfur vulcanizing agent ranges from about 0.1 to about 5 phr with a range of from about 0.5 to about 2 being preferred.

Conventional rubber additives may be incorporated in the rubber stock of the present invention. The additives commonly used in rubber stocks include fillers, plasticizers, waxes, processing oils, retarders, antiozonants, antioxidants and the like. The total amount of filler that may be used may range from about 30 to about 150 phr, with a range of from about 45 to about 100 phr being preferred. Fillers include clays, calcium carbonate, calcium silicate, titanium dioxide and carbon black. Representative carbon blacks that are commonly used in rubber stocks include N110, N121, N220, N231, N234, N242, N293, N299, S315, N326, N330, M332, N339, N343, N347, N351, N358, N375, N472, N539, N582, N630, N642, N660, N754, N762, N765, N774, N990 and N991. Plasticizers are conventionally used in amounts ranging from about 2 to about 50 phr with a range of about 5 to about 30 phr being preferred. The amount of plasticizer used will depend upon the softening effect desired. Examples of suitable plasticizers include aromatic extract oils, petroleum softeners including asphaltenes, pentachlorophenol, saturated and unsaturated hydrocarbons and nitrogen bases, coal tar products, cumarone-indene resins and esters such as dibutyl phthalate and tricresol phosphate. Common waxes which may be used include paraffinic waxes and microcrystalline blends. Such waxes are used in amounts ranging from about 0.5 to 3 phr. Materials used in compounding which function as an accelerator-activator includes metal oxides such as zinc oxide and magnesium oxide which are used in conjunction with acidic materials such as fatty acid, for example, stearic acid, oleic acid and the like. The amount of the metal oxide may range from about 1 to about 14 phr with a range of from about 2 to about 8 phr being preferred. The amount of fatty acid which may be used may range from about 0 phr to about 5.0 phr with a range of from about 0 phr to about 2 phr being preferred.

Accelerators are used to control the time and/or temperature required for vulcanization and to improve the properties of the vulcanizate. In one embodiment, a single accelerator system may be used; i.e., primary accelerator. The primary accelerator(s) may be used in total amounts ranging from about 0.5 to about 4, preferably about 0.8 to about 2.0, phr. In another embodiment, combinations of a primary and a secondary accelerator might be used with the secondary accelerator being used in a smaller, equal or greater amount to the primary accelerator. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. Preferably, the primary accelerator is a sulfenamide. If a second accelerator is used, the secondary accelerator is preferably a guanidine, dithiocarbamate or thiuram compound.

The rubber compounds of the present invention may also contain a cure activator. A representative cure activator is methyl trialkyl ($C_8$–$C_{10}$) ammonium chloride commercially available under the trademark Adogen® 464 from Sherex Chemical Company of Dublin, Ohio. The amount of activator may be used in a range of from 0.05 to 5 phr.

Siliceous pigments may be used in the rubber compound applications of the present invention, including pyrogenic and precipitated siliceous pigments (silica), although precipitate silicas are preferred. The siliceous pigments preferably employed in this invention are precipitated silicas such as, for example, those obtained by the acidification of a soluble silicate, e.g., sodium silicate. Such silicas might be characterized, for example, by having a BET surface area, as measured using nitrogen gas, preferably in the range of about 40 to about 600, and more usually in a range of about 50 to about 300 square meters per gram. The BET method of measuring surface area is described in the *Journal of the American Chemical Society*, Volume 60, page 304 (1930). The silica may also be typically characterized by having a dibutyl phthalate (DBP) absorption value in a range of about 100 to about 400, and more usually about 150 to about 300. The silica might be expected to have an average ultimate particle size, for example, in the range of 0.01 to 0.05 micron as determined by the electron microscope, although the silica particles may be even smaller, or possibly larger, in size. Various commercially available silicas may be considered for use in this invention such as, only for example herein, and without limitation, silicas commercially available from PPG Industries under the Hi-Sil trademark with designations 210, 243, etc; silicas available from Rhone-Poulenc, with, for example, designations of Z1165MP and Z165GR and silicas available from Degussa AG with, for example, designations VN2 and VN3, etc. Generally speaking, the amount of silica may range from 5 to 120 phr. The amount of silica will generally range from about 5 to 120 phr. Preferably, the amount of silica will range from 10 to 30 phr.

A class of compounding materials known as scorch retarders are commonly used. Phthalic anhydride, salicylic acid, sodium acetate and N-cyclohexyl thiophthalimide are known retarders. Retarders are generally used in an amount ranging from about 0.1 to 0.5 phr.

Conventionally, antioxidants and sometimes antiozonants, hereinafter referred to as antidegradants, are added to rubber stocks. Representative antidegradants include monophenols, bisphenols, thiobisphenols, polyphenols, hydroquinone derivatives, phosphites, thioesters, naphthyl amines, diphenyl-p-phenylenediamines, diphenylamines and other diaryl amine derivatives, para phenylenediamines, quinolines and mixtures thereof. Specific examples of such antidegradants are disclosed in The Vanderbilt Rubber Handbook (1990), pages 282–286. Anti degradants are generally used in amounts from about 0.25 to about 5.0 phr with a range of from about 1.0 to about 3.0 ph being preferred.

The rubber compound of the present invention may b used as a wire coat or bead coat for use in a tire. Any of th cobalt compounds known in the art to promote the adhesio of rubber to metal may be used. Thus, suitable coba compounds which may be employed include cobalt salts of fatty acids such as stearic, palmitic, oleic, linoleic and th like; cobalt salts of aliphatic or alicyclic carboxylic acic having from 6 to 30 carbon atoms; cobalt chloride, coba naphthenate, cobalt neodecanoate, cobalt carboxylate and a organo-cobalt-boron complex commercially available und the designation Manobond C from Wyrough and Loser, In Trenton, N.J. Manobond C is believed to have the structur

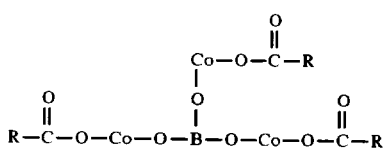

in which R is an alkyl group having from 9 to 12 carbon atoms.

Amounts of cobalt compound which may be employed depend upon the specific nature of the cobalt compound selected, particularly the amount of cobalt metal present in the compound. Since the amount of cobalt metal varies considerably in cobalt compounds which are suitable for use, it is most appropriate and convenient to base the amount of the cobalt compound utilized on the amount of cobalt metal desired in the finished stock composition.

The amount of the cobalt compound may range from about 0.1 to 2.0 phr. Preferably, the amount of cobalt compound may range from about 0.5 to 1.0 phr. When used, the amount of cobalt compound present in the stock composition should be sufficient to provide from about 0.01 percent to about 0.35 percent by weight of cobalt metal based upon total weight of the rubber stock composition with the preferred amounts being from about 0.03 percent to about 0.2 percent by weight of cobalt metal based on total weight of skim stock composition.

The sulfur vulcanizable rubber compound is cured at a temperature ranging from about 125° C. to 180° C. Preferably, the temperature ranges from about 135° C. to 160° C.

The mixing of the rubber compound can be accomplished by methods known to those having skill in the rubber mixing art. For example, the ingredients are typically mixed in at least two stages, namely at least one non-productive stage followed by a productive mix stage. The final curatives are typically mixed in the final stage which is conventionally called the "productive" mix stage in which the mixing typically occurs at a temperature, or ultimate temperature, lower than the mix temperature(s) of the preceding non-productive mix stage(s). The terms "non-productive" and "productive" mix stages are well known to those having skill in the rubber mixing art.

The polysulfide of Formula I may be compounded in either the productive or nonproductive stock. Preferably, the polysulfide of Formula I is compounded in the productive stock because of its tendency to accelerate cure of the rubber to which it is added and, therefore, function as part of a cure package. Incorporation of the polysulfide of Formula I into the rubber may be accomplished by conventional means of mixing such as by the use of a Banbury or Brabender.

The rubber composition may be used in forming a composite with reinforcing material such as in the manufacture of tires, belts or hoses. Preferably, the composition of the present invention is in the form of a tire and more specially as a component of a tire, including, the tread, wirecoat, beadcoat and plycoat.

In the following examples, the dynamic mechanical properties of cured rubber compounds were measured using a RDS II Dynamic Mechanical tester from Rheometrics, Inc. with 25 mm parallel plates in a rotational shear mode. The samples were cured at 150° C. for 27 minutes between the two plates. Storage and shear modulus, G' and tan delta were measured from 0.1 to 50 percent strain levels. The ML 1+4 @ 100° C. was measured in accordance with ASTM D1646.

The following examples are presented in order to illustrate but not limit the present invention.

EXAMPLE 1

Preparation of a Polysulfide of Formula I

A 2-liter round-bottom flask was charged with 99 g (1.0 mole) of N-methylpyrrolidinone and 101 g (1.0 mole) of triethylamine in 250 ml of toluene. The solution was stirred under an atmosphere of nitrogen as 67.5 (0.5 mole) of sulfur monochloride was added dropwise. The temperature of the exothermic reaction was held at 50° C. by the dropwise addition rate of about 1 hour. The reaction was held at 55° C. with stirring for an additional 40 minutes. The reaction mixture was treated with 500 ml of toluene, stirred and treated with 700 ml of water. The organic layer was phase-separated and stripped of volatiles to give 26.5 g of a brown solid melting at 60°–111° C. and giving a sulfur analysis of 81 percent by weight. The NMR spectrum is consistent with the structure of Formula I.

EXAMPLE 2

Physical Testing

Table 1 below shows the basic rubber compound that was used in this example. The rubber compound was prepared in a two-stage Banbury mix. All parts and percentages are by weight unless otherwise noted.

All samples were prepared with the same procedure and ingredients except as to the using the respective amount (phr) of components listed in Table 2. The physical data for each sample is also listed in Table 2.

TABLE 1

|  | (phr) |
| --- | --- |
| Non-Productive |  |
| Natural Rubber | 100.0 |
| Carbon Black (N121) | 49.0 |
| Polysulfide of Example 1 | Varied |
| Zinc Oxide | 4.0 |
| Stearic Acid | 2.0 |
| Wax | 1.5 |
| Antioxidant | 2.0 |
| Productive |  |
| Sulfur | Varied |
| Accelerator[1] | .8 |

[1]N-tert-butyl-2-benzothiazole sulfenamide

TABLE 2

| Sample | 1 | 2 | 3 | 4 |
| --- | --- | --- | --- | --- |
| Polysulfide of Ex. 1 (phr) | 0 | .5 | 1.0 | 2.0 |
| Sulfur (phr) | 1.0 | .7 | .4 | 0 |
| ML 1 + 4 @ 100° C. | 46.0 | 44.5 | 88.0 | 112.0 |
| G' @ 3%, 60° C. (MPa) | 2.30 | 1.98 | 2.10 | 2.26 |
| Tan Delta @ 3%, 60° C. | 0.196 | 0.163 | 0.139 | 0.125 |
| G' @ .2% (MPa) | 4.01 | 2.99 | 2.95 | 2.90 |
| G' @ 20% (MPa) | 1.44 | 1.34 | 1.49 | 1.66 |
| G' @ 2%/G' @ 20% | 2.79 | 2.23 | 1.98 | 1.75 |
| t90 (min.) | 13.42 | 9.11 | 6.21 | 4.96 |

The above results show that, as the amount of the polysulfide of N-methylpyrrolidinone increases (with a decrease in added sulfur), the Mooney viscosity of the compounds increase indicating an increase in rubber stiffness with a concomitant decrease in Tan Delta values at 3 percent and 60° C. A decrease in Tan Delta values at 3 percent and 60° C. indicates a decrease in rubber hysteresis which predicts cooler running and lowered rolling resistance when used in tire treads. The lowered G' ratio indicates improved rubber-to-filler interaction and better filler dispersion.

EXAMPLE 3

Physical Testing

Table 3 below shows the basic rubber compound that was used in this example. The rubber compound was prepared in a two-stage Banbury mix. All parts and percentages are by weight unless otherwise noted.

All samples were prepared with the same procedure and ingredients except as to the respective amount (phr) of components listed in Table 4. The physical data for each sample is also listed in Table 4.

TABLE 3

|  | (phr) |
| --- | --- |
| Non-Productive |  |
| Emulsion Polymerized SBR[1] | 100.0 |
| Carbon Black (N299) | 50.0 |
| Polysulfide of Example 1 | Varied |
| Stearic Acid | 2.0 |
| Naphthenic Oil | 5.0 |
| Wax | 1.5 |
| Zinc Oxide | 3.0 |
| Productive |  |
| Sulfur | Varied |
| Accelerator[2] | 1.5 |
| Antioxidant | 2.5 |

[1]Commercially available from The Goodyear Tire & Rubber Company as Plioflex ® 1502.
[2]N-cyclohexyl benzothiazole-2-sulfenamide

TABLE 4

| Sample | 1 | 2 | 3 | 4 |
| --- | --- | --- | --- | --- |
| Polysulfide of Ex. 1 (phr) | 0 | .5 | 1.0 | 2.0 |
| Sulfur (phr) | 1.4 | 1.1 | 0.8 | 0.2 |
| ML 1 + 4 @ 100° C. | 36 | 49 | 57.5 | 93 |
| G' @ 3%, 60° C. (MPa) | 1.37 | 1.40 | 1.53 | 1.92 |
| Tan Delta @ 3%, 60° C. | 0.150 | 0.137 | 0.149 | 0.135 |
| G' @ .2% (MPa) | 1.88 | 1.88 | 2.18 | 2.60 |
| G' @ 20% (MPa) | 1.01 | 1.06 | 1.12 | 1.38 |
| G' @ 2%/G' @ 20% | 1.85 | 1.79 | 1.94 | 1.88 |

The data in Table 4, similar to the data in Table 2, shows that, with increasing levels of the polysulfide of N-methylpyrrolidinone (with a decrease in added sulfur), the Mooney viscosity of the compounds increase with a concomitant decrease in Tan Delta value at 3 percent and 60° C.

EXAMPLE 4

Physical Testing

Table 5 below shows the basic rubber compound that was used in this example. The rubber compound was prepared in a two-stage Banbury mix. All parts and percentages are by weight unless otherwise noted.

All samples were prepared with the same procedure and ingredients except as to the using the respective amount (phr) of components listed in Table 6. The physical data for each sample is also listed in Table 6.

TABLE 5

|  | (phr) |
| --- | --- |
| Non-Productive |  |
| Emulsion Polymerized SBR[1] | 100.0 |
| Carbon Black (N299) | 50.0 |
| Polysulfide of Example 1 | Varied |
| Stearic Acid | 0.5 |
| Napthenic Oil | 5.0 |
| Wax | 1.5 |
| Zinc Oxide | 3.0 |
| Productive |  |
| Sulfur | 1.4 |
| Accelerator[2] | 1.5 |
| Antioxidant | 2.5 |
| Stearic Acid | 1.5 |

[1]Commericially available from The Goodyear Tire & Rubber Company as Pliofex ® 1502.
[2]N-tert-butyl-2-benzothiazole sulfenamide

TABLE 6

| Sample | 1 | 2 |
| --- | --- | --- |
| Polysulfide of Ex. 1 (phr) | 0 | 2.0 |
| ML 1 + 4 @ 100° C. | 62 | 88 |
| G' @ 3%, 60° C. (MPa) | 2.04 | 3.04 |
| Tan Delta @ 3%, 60° C. (MPa) | 0.165 | 0.096 |
| G' @ 0.2% (MPa) | 2.63 | 3.72 |
| G' @ 20% (MPa) | 1.59 | 2.45 |
| G' @ 2%/G' @ 20% | 1.66 | 1.16 |

The above data shows that, with increasing levels of the polysulfide of N-methylpyrrolidinone (with the level of sulfur held constant), the Mooney viscosity of the compound increases with a concomitant decrease in Tan Delta at percent and 60° C.

What is claimed is:

1. A compound of the formula:

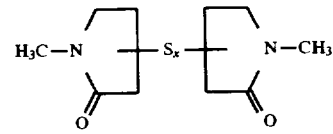

where x is an integer of from 2 to 30.

2. The compound of claim 1 wherein x is an integer from 3 to 15.

3. A vulcanized rubber composition comprising a sulfur vulcanized rubber and from about 0.1 to about 10 phr of pl of the formula:

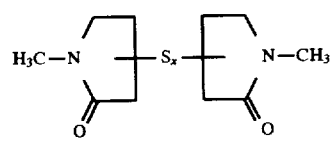

where x is an integer of from 2 to 30.

4. The composition of claim 3 wherein said composition additionally comprises from 30 to 150 phr of carbon black 5. The composition of claim 3 wherein said composition additionally comprises from 5 to 120 phr of silica.

6. The composition of claim 3 wherein the rubber selected from the group consisting of natural rubber, synthetic cis polyisoprene, polychloroprene, polybutadiene butyl rubber, halobutyl rubber, styrene/butadiene copolymer rubber, isoprene/butadiene copolymer rubber, terpolymer of acrylonitrile, butadiene and styrene, and mixtures thereof 7. The composition of claim 6 wherein the rubber is natural rubber.

8. The composition of claim 6 wherein the rubber is styrene/butadiene copolymer rubber.

9. The composition of claim 6 which in the form of a composite selected from the group consisting of a tire, belt or hose.

10. The composition of claim 9 which is in form of a tire

11. The composition of claim 10 wherein the composition is in a component of a tire selected from the group consisting of a tread, wirecoat, beadcoat and plycoat.

* * * * *